United States Patent [19]
Balbierz et al.

[11] Patent Number: 6,033,393
[45] Date of Patent: Mar. 7, 2000

[54] METHOD AND APPARATUS FOR OVERPRESSURE PROTECTION OF A CATHETER

[75] Inventors: Daniel J. Balbierz, Redwood City; Jack Walker, Portola Valley, both of Calif.

[73] Assignee: Johnson & Johnson Medical, Inc., Arlington, Tex.

[21] Appl. No.: 08/775,409

[22] Filed: Dec. 31, 1996

[51] Int. Cl.[7] .................................................. A61M 31/00
[52] U.S. Cl. .................... 604/508; 604/247; 604/264; 604/523; 604/266
[58] Field of Search ...................... 604/264, 280, 604/53, 49, 48, 118, 245, 247, 96, 284, 266, 267; 606/191–198

[56] References Cited

U.S. PATENT DOCUMENTS

| | | | |
|---|---|---|---|
| 3,856,010 | 12/1974 | Moorehead et al. | 128/214.4 |
| 4,351,341 | 9/1982 | Goldberg et al. | 128/348 |
| 4,502,502 | 3/1985 | Krug | 137/512.3 |
| 4,551,130 | 11/1985 | Herbert et al. | 604/32 |
| 4,624,659 | 11/1986 | Goldberg et al. | 604/121 |
| 4,669,465 | 6/1987 | Moore et al. | 128/303.1 |
| 4,701,166 | 10/1987 | Groshong et al. | 604/247 |
| 5,186,431 | 2/1993 | Tamari | 251/5 |
| 5,305,982 | 4/1994 | Tamari | 251/5 |
| 5,336,051 | 8/1994 | Tamari | 417/19 |
| 5,437,632 | 8/1995 | Engelson | 604/53 |
| 5,683,345 | 11/1997 | Waksmon | 600/3 |

FOREIGN PATENT DOCUMENTS

WO94/02195  2/1994  WIPO .

*Primary Examiner*—Corrine McDermott
*Assistant Examiner*—N. Kent Gring
*Attorney, Agent, or Firm*—Blakely, Sokoloff, Taylor & Zafman

[57] ABSTRACT

A method and apparatus for overpressure protection of a catheter from an indwelling catheter. A method in one embodiment includes injecting an agent into the catheter and relieving overpressures in the catheter during the injecting step. The agent is typically a declotting agent and the obstruction is typically a clot (e.g., blood clot). In one embodiment of the apparatus, a catheter includes a cannula and a first hub and a second hub, each of which are coupled to the cannula. The first hub is for receiving an agent which is placed into the cannula to remove an obstruction, and the second hub includes an overpressure relief valve for relieving an overpressure condition in the cannula. Other embodiments of the invention are also described.

13 Claims, 3 Drawing Sheets

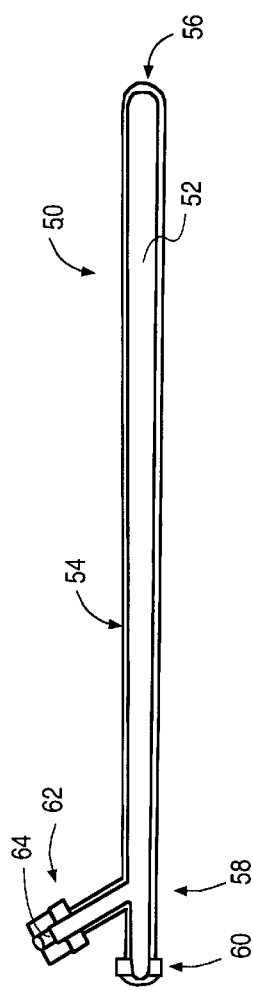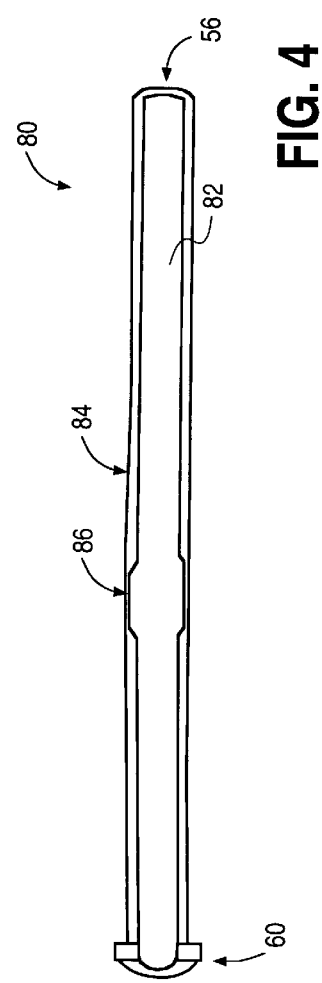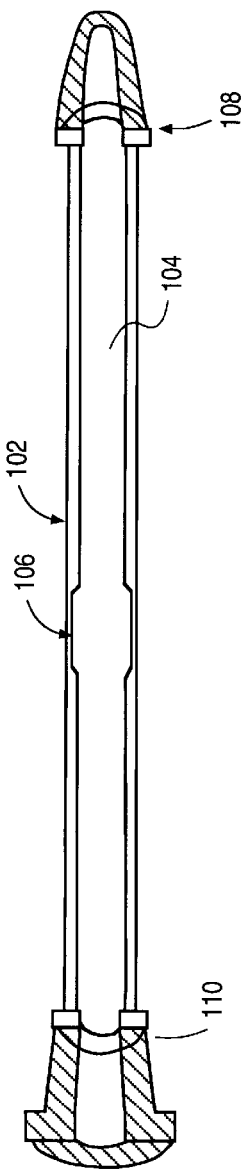

METHOD AND APPARATUS FOR OVERPRESSURE PROTECTION OF A CATHETER

BACKGROUND OF THE INVENTION

1. Field of the Invention

The invention is generally directed to medical catheters and more specifically to circumstances arising when a catheter which is in place in a patient becomes obstructed.

Catheters are commonplace in the medical field and have a variety of uses. The term "catheter" is commonly used to identify a tubular instrument that is inserted into a body cavity or orifice, naturally or surgically opened. Vascular catheters, for example, come in many different forms and have many different uses. A vascular catheter typically consists of a hub and tubing or cannula through which fluid flows. The hub may include a flash chamber that allows the individual placing the catheter to see blood in the flash chamber that indicates the catheter has entered a vein.

Often, a catheter which has been placed into a blood vessel will become obstructed. There are many ways in which a catheter becomes obstructed. The most common obstruction is typically a blood clot which forms in the lumen of the catheter and clogs the fluid flow through the catheter. These clots often occur in catheters which remain in a patient for an extended period of time. Because of the difficulty inserting such catheters into a patient, it is often desirable to avoid inserting a new catheter into the patient when a catheter becomes obstructed. Consequently, a typical technique in the prior art for dealing with an obstructed catheter is to declot the catheter by adding a declotting agent to the catheter. Typically, this declotting agent will dissolve the blood clot and thereby remove the obstruction from the catheter. The declotting agent may also be a simple saline solution. FIG. 1 shows an example in the prior art of a catheter 10 which has been inserted into the vein 12 of a patient's limb 14. While indwelling in the patient during a period of time, a clot 16 has formed in the catheter 10 thereby obstructing the flow of fluid 18 through the catheter. During normal operation without the clot 16, the catheter 10 conveys the fluid 18 through hub 20 and through the catheter 10 to the distal end 8 of the catheter thereby providing the fluid 18 into the vasculature of the patient. However, when the clot forms the fluid flow becomes obstructed, and this poses a problem for the treatment of the patient.

FIG. 2 shows a typical approach in the prior art to remove the clot 16 by using a declotting solution 26 which is contained within a syringe 22 which has been attached to the hub 20 of the catheter 10. It will be appreciated that this procedure typically involves disconnecting the hub 20 from the fluid feed connection and supply and inserting the syringe 22 into the hub. The declotting solution 26 is introduced into the catheter 10 by applying pressure to the plunger 24 of the syringe 22. One of the dangers of this procedure is the potential high pressures created during the declotting process. A small syringe can easily generate pressures in excess of 100 psi which can rupture the catheter or dislodge the clot downstream into the patient's vasculature. Often, care is taken to try to eliminate this danger by carefully premeasuring the volume of declotting agent to be instilled into the catheter. However, there are inherent uncertainties involved in premeasuring this volume because the clinician has no assurance of the exact location of the clot, and hence the volume of the declotting agent to be used. Too much volume of the declotting agent will often lead to either rupture of the catheter or dislodging of the clot into the patient's vasculature.

Thus, it is desirable to provide a method to prevent overpressurization of a catheter during a declotting process or whenever the potential for overpressurization of a catheter exists.

SUMMARY OF THE INVENTION

A method and apparatus are disclosed for overpressure protection of a catheter such as an indwelling catheter. An embodiment of a method according to the invention includes injecting an agent into the catheter and relieving overpressures in the catheter during the injecting step. The agent is typically a declotting agent and the obstruction is typically a clot, such as a blood clot.

According to one embodiment of the apparatus of the present invention, the catheter includes a cannula and a first hub and a second hub, each of which are coupled to the cannula. The first hub is for receiving an agent which is placed into the cannula to remove an obstruction, and the second hub includes an overpressure relief valve for relieving an overpressure condition in the cannula.

In another embodiment of the apparatus of the present invention, a catheter includes a cannula having a distal end for insertion into a patient and a proximal end to be located outside of the patient. This cannula has a first portion and a second portion, where the second portion is near the proximal end and is expandable to relieve an overpressure condition in the cannula. A hub is typically coupled to the cannula, and this hub is for receiving an agent which is placed into the cannula to remove an obstruction in the cannula.

In another embodiment of the present invention, an extension for a catheter is provided wherein the extension includes a cannula having a distal end for coupling to the catheter and a proximal end. This extension further includes a hub coupled to the cannula for receiving an agent which is placed into the cannula to remove an obstruction in the catheter and further includes either a second hub having an overpressure relief valve or a portion of the cannula which is expandable in order to relieve an overpressure condition in the catheter.

Additional features and benefits of the invention will become apparent from the detailed description, figures and claims as set forth below.

DESCRIPTION OF THE DRAWINGS

FIG. 3 shows a cross-sectional view of a catheter according to one embodiment of the present invention.

FIG. 4 shows a cross-sectional view of a catheter according to another embodiment of the present invention.

FIG. 5A shows a cross-sectional view of an extension for a catheter according to another embodiment of the present invention.

FIG. 6A shows a closed state, and FIG. 6B shows the valve in an opened state.

DETAILED DESCRIPTION

Figure 1:
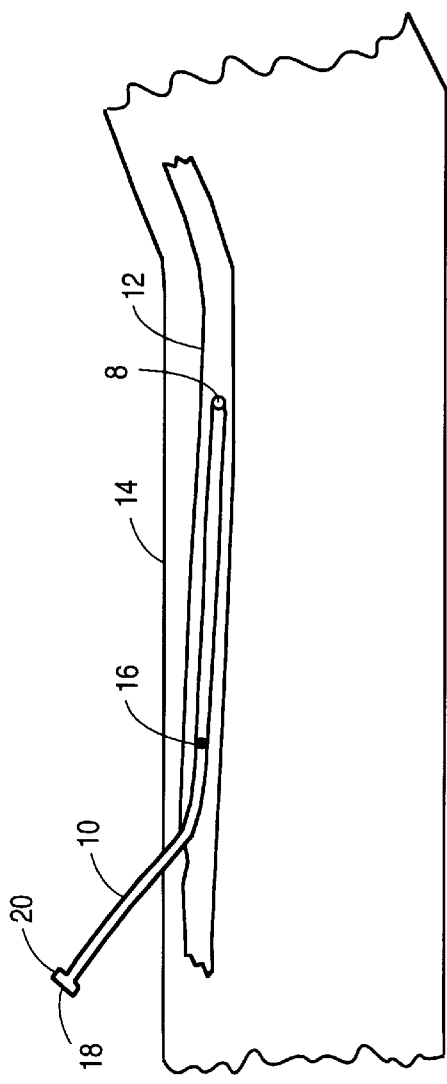
FIG. 1 illustrates a catheter indwelling in a vein of a patient's limb.
Figure 2:
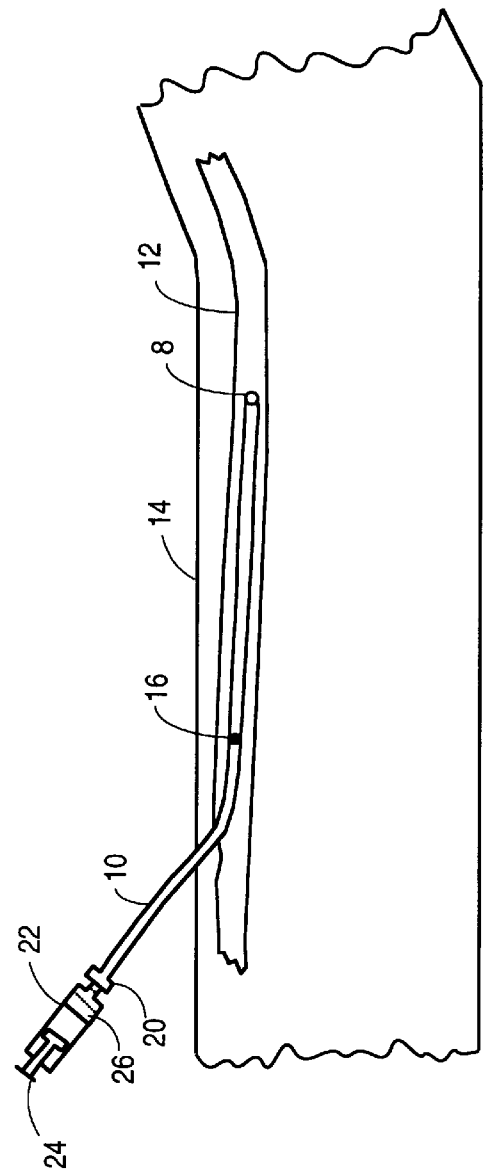
FIG. 2 shows a prior art technique for declotting an obstructed indwelling catheter.

The invention relates to a method and apparatus for controlling overpressure conditions in a catheter when removing an obstruction from the catheter. In the following detailed description, specific embodiments of the invention are described with reference to particular examples. Numerous specific details are set forth such as specific configurations, etc. It will be appreciated upon reference to this specification that these specific details need not be employed to practice the invention. In other instances, well-known materials or methods have not been described in order to avoid unnecessarily obscuring the invention.

FIG. 3 illustrates one embodiment of a catheter according to the present invention. The catheter 50 includes a hollow lumen 52 which is surrounded by the catheter's flexible cannula or tube 54. The distal end 56 of the catheter 50 is typically open in order to provide fluid flow from the distal end of the catheter into the patient's vasculature (or alternatively to drain fluids from the patient such that the flow is into the distal end of the catheter). Typically the distal end will be inserted into a patient such that during use of the catheter the distal end will remain within the patient. The proximal end 58 of the catheter 50 will remain outside of the patient, and it includes hubs 60 and 62. The hub 60 is typically used to connect to fluid supply sources (e.g., nutrients or medications) and may also be used (after disconnecting the fluid supply source) to receive a declotting agent which is placed into the catheter to remove an obstruction in the catheter. The hub 60 is coupled to the cannula of the catheter 50 and is typically designed to connect to other connecting devices such as leur locks, etc. as is well-known in the art. The hub 62 includes a overpressure relief valve 64 which is designed to relieve an overpressure condition when the declotting agent is introduced into the cannula of the catheter 50. Typically, this overpressure condition causes the relief valve to open when the pressure in the cannula exceeds a predetermined pressure.

Figure 6B:
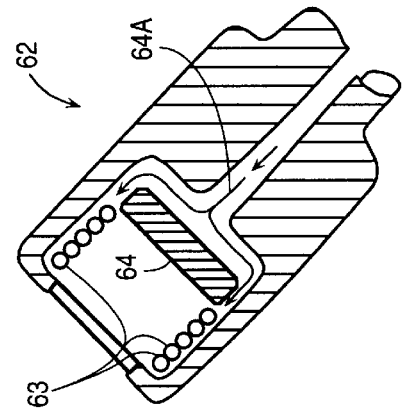
FIGS. 6A and 6B show cross-sectional views of an overpressure relief valve.
Figure 6A:
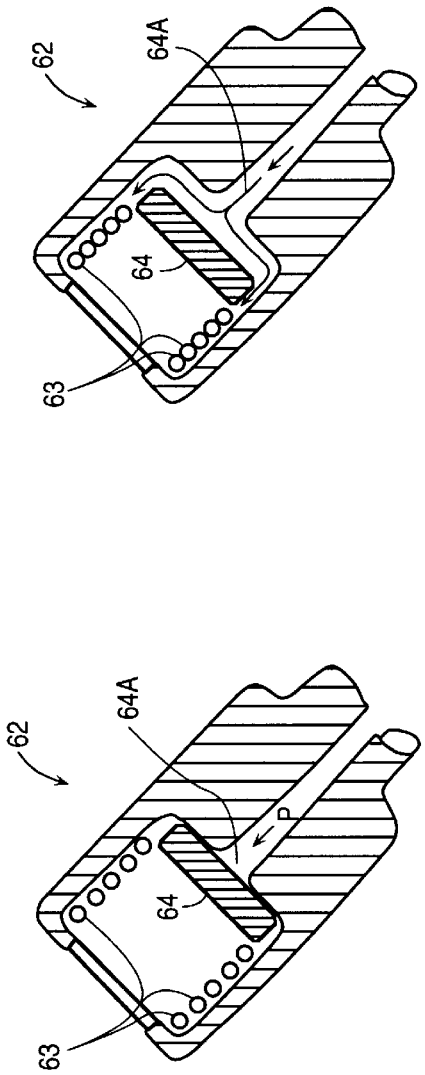

FIGS. 6A and 6B show cross-sectional views of an embodiment of an overpressure relief valve of the invention. The overpressure relief valve 64 is housed within a hollow cylindrical chamber in the hub 62. The spring 63, which is also housed within the hollow cylindrical chamber in the hub 62, provides a constant spring force Fs against the valve 64 which keeps the valve 64 closed shut against an orifice 64a. The valve is designed to open at a desired pressure "P" by designing the spring force "Fs" and the area "A" of the pressure applied against the valve 64 such that Fs=P×A. It will be appreciated that other types of valve mechanisms may be utilized to provide the overpressure relief.

The catheter of FIG. 3 is safer to declot than the catheter shown in FIG. 1 because the overpressure relief valve 64 in the hub or housing 62 will relieve any overpressure conditions which occur when the clinician instills a declotting agent into the catheter 50 by using a syringe coupled to the hub 60. Any overpressure which occurs during the instilling of the declotting agent will be relieved by the overpressure relief valve 64 such that the catheter will not rupture and the clot will not tend to be dislodged downstream into the patient's vasculature. This ensures constant pressure on the clot by the declotting agent and at the same time provides protection from overpressure of the catheter itself.

FIG. 4 shows another embodiment of a catheter according to the present invention. In this embodiment, the catheter 80 includes a flexible tube 84 which defines an inner lumen 82. The flexible tube 84 includes a reduced wall thickness region 86 which is situated along the length of the catheter such that this region will be outside of the patient during normal indwelling use of the catheter. Thus, the reduced wall thickness region 86 will be located sufficiently far away from the distal end 56 of the catheter 80. Typically, this reduced thickness region 86 will be placed near the proximal end which includes the hub 60. During normal use, the hub 60 is coupled to a fluid supply connector or to some other connector means for providing fluids to the patient or receiving fluids from the patient. During declotting, the fluid supply connector is disconnected from the hub 60, and a syringe with declotting solution is coupled to the hub 60.

An alternative to the catheter shown in FIG. 4 utilizes a different material in the region 86 rather than a reduced wall thickness region. This different material is more pliable than the other material used to form the catheter 80 such that this region will expand upon overpressure conditions in the catheter 80. In the case where the region 86 has a thinner wall thickness than the remainder of the catheter 80, the wall thickness will typically be such that this region will readily expand in an overpressure condition and thereby relieve the overpressure condition in the catheter.

Yet another alternative to the catheter shown in FIG. 4 utilizes a larger diameter tubing along a portion of the catheter which is designed to relieve pressure. The large diameter section provides overpressure protection and relief because it provides more internal surface area which effectively reduces the force applied to the wall of the catheter along this portion having the larger diameter.

FIG. 5A shows another embodiment of the present invention which is an extension to a catheter which is in place in a patient. The extension 100 includes a hub 108 which is for coupling to a hub on the catheter in use in the patient. At the other end of the catheter 100 is the hub 110 which is intended to be used to connect to a syringe or other device for introducing a declotting agent into the extension and to thereby introduce the declotting agent into the catheter which is coupled to the extension 100. The catheter 100 includes a lumen 104 defined by the tube 102 which includes a reduced wall thickness region 106 which functions and may be constructed in the same way as the reduced wall thickness region 86 shown in FIG. 4. The reduced wall thickness region 106 provides for overpressure relief in the extension 100 which accordingly provides overpressure relief in the indwelling catheter which is connected to the extension 100 through the hub 108.

The extension 100 or other extensions described herein provide an advantage with respect to existing supplies of prior art catheters. That is, these extensions may be used with existing prior art catheters to declot the prior art catheters while providing overpressure protection for these prior art catheters. The extension is attached to a hub at the proximal end of a prior art indwelling catheter and then the declotting agent is added through the extension into the prior art catheter while at the same time providing overpressure protection for the prior art catheter.

Figure 5B:
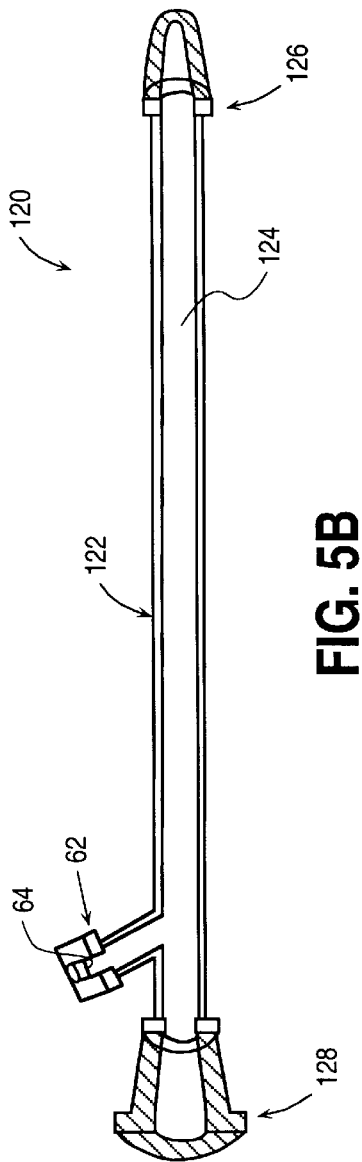
FIG. 5B shows a cross-sectional view of another extension for a catheter according to another embodiment of the present invention.

FIG. 5B shows another embodiment of an extension for a catheter according to the present invention. The extension 100 includes a tube 122 which defines a hollow lumen 124. The extension 120 includes a hub 126 at a distal end of the catheter 120 and a hub 128 at the proximal end of a catheter. The hub 126 is for coupling to a hub on the proximal end of an indwelling catheter in order to provide the declotting agent through the extension 120 to the indwelling catheter which is obstructed. The hub 128 is for connection to a syringe or other device which may be used to introduce a declotting agent into the extension 120 and thereby into the indwelling catheter which is coupled to the extension 120. The catheter 120 also includes a hub 62 which includes an overpressure relief valve 64 which is similar to the overpressure relief valve 64 shown in FIG. 3.

The foregoing invention has been described with reference to various configurations and materials which may be used with the catheters and extensions of the present invention. It will be appreciated that various embodiments of the catheters and extensions of the present invention may be constructed from the same materials used to construct prior art catheters. Moreover, the hubs used on the catheters and extensions of the present invention may be similar to the hubs used on prior art catheters.

What is claimed is:

1. A method for preventing overpressurization in a catheter when eliminating an obstruction in said catheter, said method comprising:

injecting an agent into said catheter, said agent being designed to eliminate said obstruction;

relieving overpressure in said catheter during said injecting step, wherein said catheter is ope-ended, wherein said catheter has a hollow lumen, and a proximal end branching into a first and second end, wherein the first end is an open end coupled to a first hub located outside of a patent, wherein the second end is coupled to a second hub having a pressure relief valve.

2. A method as in claim 1 wherein said hollow lumen has an open distal end and said catheter is in place in a patient and said obstruction is a clot and said agent is a declotting agent.

3. A method as in claim 2 wherein said pressure relief valve is located outside of said patient and said pressure relief valve opens when overpressure in said catheter occurs.

4. A method for preventing overpressurization in a catheter when eliminating an obstruction in said catheter, said method comprising:

injecting an agent into said catheter, said agent being designed to eliminate said obstruction;

relieving overpressure in said catheter during said injecting step, said catheter using a thin-walled portion expanding to relieve overpressure in said catheter.

5. A method as in claim 4 wherein said hollow lumen has an open proximal end and said declotting agent is injected into said hollow lumen through said open proximal end.

6. A method as in claim 2 further comprising:

adding an extension onto said catheter, said extension receiving said declotting agent and conveying said declotting agent to said catheter and relieving said overpressure.

7. An extension for a catheter, said extension comprising:

a cannula having a distal end for coupling to said catheter and a proximal end;

a hub coupled to said proximal end, said hub for receiving an agent which is placed into said cannula to remove an obstruction in said catheter, said cannula having at least a portion thereof which is expandable or expanded to relieve an overpressure condition in said catheter, wherein said catheter is open-ended.

8. An extension as in claim 7 wherein said obstruction is a clot and said agent is a declotting agent.

9. An extension as in claim 8 further comprising a further hub coupled to said distal end, said further hub for coupling said extension to said catheter.

10. An extension as in claim 8 wherein said overpressure condition occurs at a predetermined pressure.

11. An extension as in claim 8 wherein said cannula comprises a first portion having a first wall thickness and said at least a portion having a second wall thickness which is less than said first wall thickness.

12. An extension as in claim 8 wherein a substantial portion of said cannula is expandable to relieve said overpressure condition.

13. An extension as in claim 8 wherein said cannula comprises a first portion formed from a first material and said at least a portion formed from a second material which is more pliable than said first material.

* * * * *

UNITED STATES PATENT AND TRADEMARK OFFICE
CERTIFICATE OF CORRECTION

PATENT NO. : 6,033,393
DATED : March 7, 2000
INVENTOR(S) : Daniel J. Balbierz and Jack Walker It is certified that error appears in the above-identified patent and that said Letters Patent are hereby corrected as shown below:

Claim I, Line 17:

"ope-ended" should be --open-ended--

Signed and Sealed this

Seventeenth Day of April, 2001

*Attest:*

NICHOLAS P. GODICI

*Attesting Officer*     *Acting Director of the United States Patent and Trademark Office*